United States Patent

Goto et al.

Patent Number: 5,344,814
Date of Patent: Sep. 6, 1994

[54] HERBIDICAL 1-(3,4-DISUBSTITUTED PHENYL) TETRAZOLINONES

[75] Inventors: Toshio Goto; Hidenori Hayakawa, both of Tochigi; Yukiyoshi Watanabe, Saitama; Akihiko Yanagi, Tochigi, all of Japan

[73] Assignee: Nihon Bayer Agrochem K.K., Tokyo, Japan

[21] Appl. No.: 67,316

[22] Filed: May 26, 1993

[30] Foreign Application Priority Data

May 28, 1992 [JP] Japan ................... 4-160083

[51] Int. Cl.$^5$ ................. A01N 43/713; C07D 257/04
[52] U.S. Cl. ..................... 504/261; 548/251
[58] Field of Search ............ 548/251; 504/261

[56] References Cited

U.S. PATENT DOCUMENTS 4,618,365 10/1986 Covey et al. .......... 548/251
4,826,529 5/1989 Covey et al. .......... 548/251
4,830,661 5/1989 Covey et al. .......... 548/251

OTHER PUBLICATIONS

CA 108(19): 163178b A QSAR Study . . . Herbicides. Bell et al., 1988, p. 241.
The Journal of Organic Chemistry, vol. 45, No. 25, 5 Dec. 1980, pp. 5130–5136.
Synthesis and Structure–Activity Relationships of 1-aryl-4-substituted-1,4-dihydro-5H-tetrazol-5-ones, a novel class of pre-and post-emergence Herbicides, Pestic. Sci. 1990, 30, 259–274.
1987 British Crop Protection Conference –Weeds 3C-9, 259-255, Bell et al., a QSAR Study of Substituted Tetrazolinone Herbicides.

Primary Examiner—Mary C. Lee
Assistant Examiner—Joseph K. McKane
Attorney, Agent, or Firm—Sprung Horn Kramer & Woods

[57] ABSTRACT

Herbicidal 1-(3,4-disubstituted phenyl)tetrazolinones of the formula

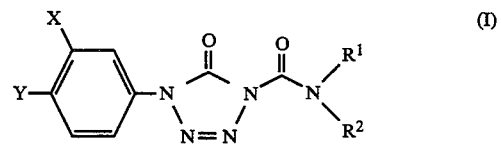

wherein
X represents halogen,
Y represents trifluoromethoxy or trifluoromethylthio,
$R^1$ represents propyl, isopropyl or allyl, and
$R^2$ represents propyl, isopropyl or allyl.

9 Claims, No Drawings

HERBIDICAL 1-(3,4-DISUBSTITUTED PHENYL) TETRAZOLINONES

The present invention relates to novel 1-(3,4-disubstituted phenyl)tetrazolinone derivatives, to a process for their preparation, and to their use as herbicides.

It has already been disclosed that a certain group of tetrazolinone derivatives is useful as herbicides (see U.S. Pat. Nos. 4,956,469, 5,003,075 and 5,019,152 or the corresponding European Applications EP-A-146,279 and EP-A-202,929).

There have now been found novel 1-(3,4-disubstituted phenyl)tetrazolinone derivatives of the formula (I)

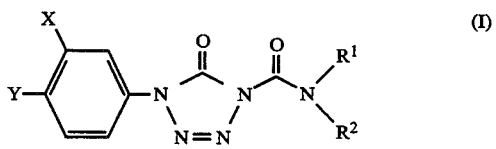

wherein
X represents halogen,
Y represents trifluoromethoxy or trifluoromethylthio,
$R^1$ represents propyl, isopropyl or allyl, and
$R^2$ represents propyl, isopropyl or allyl.

1-(3,4-disubstituted phenyl)tetrazolinone derivatives of the formula (I) are obtained when compounds of the formula (II)

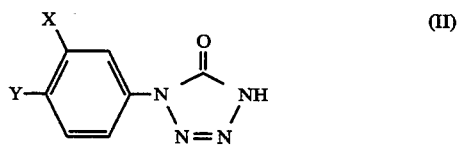

wherein X and Y have the above mentioned meanings,
are reacted with compounds of the formula (III)

wherein $R^1$ and $R^2$ have the above mentioned meanings, and $R^3$ represents a releasable group such as chlorine or bromine,
if appropriate, in the presence of acid binders, and in the presence of an inert solvent.

The novel 1-(3,4-disubstituted phenyl)tetrazolinone derivatives of the formula (I) exhibit powerful herbicidal properties, particularly against paddy-field weeds.

Surprisingly, the 1-(3,4-disubstituted phenyl)tetrazolinone derivatives according to the invention exhibit a substantially greater selective herbicidal action on paddy-field weeds than the compounds known from the relevant prior art, (for instance, the aforementioned U.S. Pat. Nos. 4,956,469, 5,003,075 and 5,019,152 or EP-A-146,279 and EP-A-202,929).

In the compounds represented by the formula (I) according to the present invention as well as in each of the general formulas representing the intermediate compounds for the production of the compounds of the present invention, halogen includes fluorine, chlorine, bromine and iodine, preferably chlorine or fluorine.

Among the 1-(3,4-disubstituted phenyl)tetrazolinone derivatives according to the invention of the formula (I), the preferred compounds are those in which
X represents fluorine or chlorine,
Y represents trifluoromethoxy or trifluoromethylthio,
$R^1$ represents propyl or allyl, and
$R^2$ represents propyl or allyl.

As compounds of the formula (I) according to the invention there may be mentioned:

1-(3-chloro-4-trifluoromethoxyphenyl)-4-(N,N-dipropylcarbamoyl)-5(4H)-tetrazolinone,
1-(3-fluoro-4-trifluoromethoxyphenyl)-4-(N,N-diallylcarbamoyl)-5(4H)-tetrazolinone,
1-(3-chloro-4-trifluoromethylthiophenyl)-4-(N,N-dipropylcarbamoyl)-5(4H)-tetrazolinone,
1-(3-fluoro-4-trifluoromethoxyphenyl)-4-(N,N-dipropylcarbamoyl)-5(4H)-tetrazolinone,
1-(3-fluoro-4-trifluoromethylthiophenyl)-4-(N,N-dipropylcarbamoyl)-5(4H)-tetrazolinone,
1-(3-bromo-4-trifluoromethoxyphenyl)-4-(N,N-dipropylcarbamoyl)-5(4H)-tetrazolinone,
1-(3-bromo-4-trifluoromethoxyphenyl)-4-(N,N-diallylcarbamoyl)-5(4H)-tetrazolinone,
1-(3-bromo-4-trifluoromethylthiophenyl)-4-(N,N-dipropylcarbamoyl)-5(4H)-tetrazolinone,
1-(3-fluoro-4-trifluoromethylthiophenyl)-4-(N,N-diisopropylcarbamoyl)-5(4H)-tetrazolinone,
1-(3-chloro-4-trifluoromethylthiophenyl)-4-(N,N-diallylcarbamoyl)-5(4H)-tetrazolinone,
1-(3-chloro-4-trifluoromethoxyphenyl)-4-(N,N-diallylcarbamoyl)-5(4H)-tetrazolinone,
1-(3-bromo-4-trifluoromethlthiophenyl)-4-(N,N-diallylcarbamoyl)-5(4H)-tetrazolinone,
1-(3-fluoro-4-trifluoromethylthiophenyl)-4-(N,N-diallylcarbamoyl)-5(4H)-tetrazolinone,
1-(3-chloro-4-trifluoromethoxyphenyl)-4-(N,N-diisopropylcarbamoyl)-5(4H)-tetrazolinone, and
1-(3-chloro-4-trifluoromethylthiophenyl)-4-(N,N-diisopropylcarbamoyl)-5(4H)-tetrazolinone.

If in the process for the preparation of the compounds of formula (I), for example, 1-(3-chloro-4-trifluoromethoxyphenyl)-5(4H)-tetrazolinone and dipropylcarbamoyl chloride are used as starting materials, the course of the reaction can be represented by the following equation:

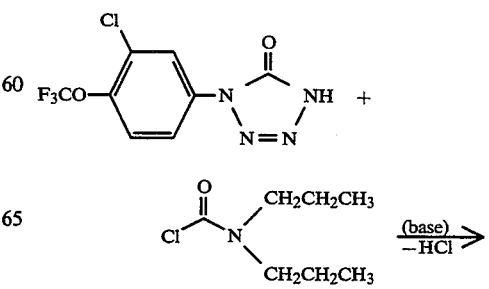

-continued

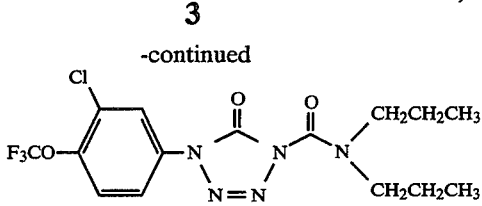

The compounds of the formula (II) can be obtained by the process disclosed, for example, in The Journal of Organic Chemistry, Vol. 45, No. 21, 1980, pages 5130–5136 or The Journal of American Chemical Society, Vol. 81, No. 7, 1980, pages 3076–3079.

As specific examples thereof, there may be mentioned:

1-(3-chloro-4-trifluoromethoxyphenyl)-5(4H)tetrazolinone,
1-(3-bromo-4-trifluoromethoxyphenyl)-5(4H)-tetrazolinone,
1-(3-fluoro-4-trifluoromethoxyphenyl)-5(4H)tetrazolinone,
1-(3-chloro-4-trifluoromethylthiophenyl)-5(4H)tetrazolinone,
1-(3-bromo-4-trifluoromethylthiophenyl)-5(4H)tetrazolinone, and
1-(3-fluoro-4-trifluoromethylthiophenyl)-5(4H)tetrazolinone.

The compounds of the formula (III) are well known in organic chemistry. As specific examples thereof, there may be mentioned:

Diisopropylcarbamoyl chloride or bromide,
Diallylcarbamoyl chloride or bromide, and
Dipropylcarbamoyl chloride or bromide.

As appropriate diluents for carrying out the process according to the invention there may be used any inert solvents.

Examples of such diluents are aliphatic, cycloaliphatic and aromatic, optionally chlorinated, hydrocarbons such as pentane, hexane, cyclohexane, petroleum ether, ligroin, benzene, toluene, xylene, methylene chloride, chloroform, carbon tetrachloride, 1,2-dichloroethane, chlorobenzene, dichlorobenzene, and the like; ethers such as diethyl ether, methyl ethyl ether, di-isopropyl ether, dibutyl ether, dioxane, dimethoxyethane (DME), tetrahydrofurane (THF), diethyleneglycol dimethylether (DGM), and the like; nitriles such as acetonitrile, propionitrile and the like; acid amides such as dimethyl formamide (DMF), dimethyl acetamide (DMA), N-methylpyrrolidone, 1,3-dimethyl-2-imidazolidinone, hexamethylphosphoric triamide (HMPA), and the like; sulfones and sulfoxides such as dimethyl sulfoxide (DMSO), sulfolane, and the like; and bases such as pyridine.

The process according to the invention is carried out preferably in the presence of an acid binder such as bases including the hydroxide, carbonate, bicarbonate and alcoholate of alkali metals and alkali metal hydrides such as, for example, sodium hydrogen carbonate, potassium hydrogen carbonate, sodium carbonate, potassium carbonate, lithium hydroxide, sodium hydroxide, potassium hydroxide, calcium hydroxide, and the like; inorganic amides of alkali metals such as lithium amide, sodium amide, potassium amide and the like, and organic bases including tertiary amines, dialkylaminoanilines and pyridines, such as, for example, triethylamine, tributylamine, 1,1,4,4-tetramethylenediamine (TMEDA), N,N-dimethylaniline, N,N-diethylaniline, pyridine, 4-dimethylaminopyridine (DMAP), 1,4-diazabicyclo[2,2,2]octane (DABCO), 1,8-diazabicyclo-[5,4,0]-undec-7-ene (DBU), and the like. Furthermore, organic lithium compounds such as methyl lithium, n-butyl lithium, sec-butyl lithium, tert-butyl lithium, phenyl lithium, dimethyl copper lithium, lithium diisopropyl amide, lithium cyclohexylisopropyl amide, lithium dicyclohexyl amide, n-butyl lithium.DABCO, n-butyl lithium.DBU, n-butyl lithium.TMEDA, and the like.

In the process according to the invention, the reaction temperature can be varied within a substantially wide range. In general, the reaction is carried out at a temperature of from about −80° C. to about 200° C., preferably from about −10° C. to about 130° C.

Further, the reaction is carried out under normal pressure, although it is also possible to employ a higher or reduced pressure.

In carrying out the process according to the invention, the desired compounds of the formula (I) can be obtained by reacting of about 1.0 to 1.3 mols of the compound of the formula (III) per mol of the compound of the formula (II), in a diluent such as acetonitrile, in the presence of 1 to 1.3 mols of acid binder.

The active compounds according to the invention can be used as defoliants, desiccants, agents for destroying broad-leaved plants and, especially, as weed killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestation, decorative tree plantings, orchards, vineyards, citrus groves, nut orchards, banana plantations, coffee plantations, tea plantations, rubber plantations, oil palm plantations, cocoa plantations, soft fruit plantings and hop-fields, and for the selective combating of weeds in annual cultures.

The active compounds can be converted into the customary formulations, such as solutions, emulsions, wettable powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products.

Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc. The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between 0.01 and 10 kg of active compound per hectare of soil surface, preferably between 0.01 and 2 kg per ha.

The preparation and use of the active compounds according to the invention can be seen from the following examples.

PREPARATION EXAMPLES

Example 1 (synthesis of starting material)

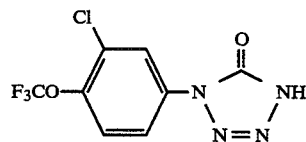

3-Chloro-4-trifluoromethoxyphenyl isocyanate (10 g) was mixed with trimethylsilyl azide (7.28 g), and the resulting mixture was heated under reflux for 8 hours. The excess trimethylsilyl azide was distilled off under reduced pressure, and to the residue thus obtained methanol (60 ml) was added. Thereafter, the methanol was distilled off, and the resultant residue was subjected to flash column chromatography, eluted by hexane:ethyl acetate=5:1, to give 1-(3-chloro-4-trifluoromethoxyphenyl)-5(4H)-tetrazolinone (8.27 g). mp. 133°–134.5° C.

Example 2

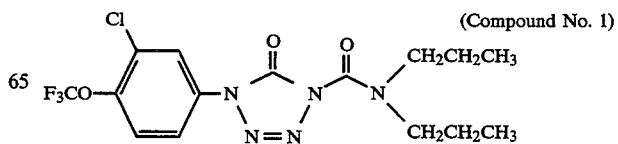

(Compound No. 1)

1-(3-chloro-4-trifluoromethoxyphenyl)-5(4H)-tetrazolinone (2 g) and potassium carbonate (1.3 g) were suspended in acetonitrile (30 ml). The resulting suspension was heated under reflux for 15 minutes. The reaction mixture was cooled and dipropylcarbamoyl chloride (1.3 g) was added. Then, the reaction mixture was heated under reflux for 5 hours. The salts were removed by filtration, and the filtrate was evaporated under reduced pressure. The resulting residue was purified by flash column chromatohraphy, eluted by hexane:ethyl acetate=7:1, to give 1-(3-chloro-4-trifluoromethoxyphenyl)-4-(N,N-dipropylcarbamoyl)-5(4H)-tetrazolinone (2.1 g). mp. 69°–72° C.

Other compounds according to the present invention similarly obtained are:

Compound No. 2: 1-(3-chloro-4-trifluoromethylthiophenyl)-4-(N,N-dipropylcarbamoyl)-5(4H)-tetrazolinone mp. 74.5°–77° C.

Compound No. 3: 1-(3-chloro-4-trifluoromethoxyphenyl)-4-(N,N-diallylcarbamoyl)-5(4H)-tetrazolinone mp. 58.8°–60° C.

Biological test

Comparative compound

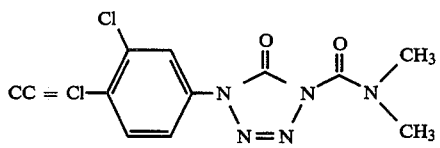

(The compound is disclosed in the above-mentioned U.S. Pat. No. 4,956,469 and EP-A's 146,279 and 202,929).

Example 3

Test on Herbicidal Activity Against Paddy-field Weeds

Formulation of Active Compounds

Carrier: 5 parts by weight of acetone

Emulsifier: 1 part by weight of benzyloxy polyglycol ether

To produce a suitable formulation of each of the active compounds, 1 part by weight of the active compound was mixed with the stated amount of carrier and with the stated amount of emulsifier, and the resulting emulsifiable concentrate was diluted with water to the desired concentration.

Test Method

Each of several pots, having a size of 25×20×9 cm and an area of 1/2,000 are, was filled with soil taken from a paddy field. Rice seedlings (Nipponbare Variety) at the 2.5-leaf stage, with a height of 15 cm, were transplanted into these pots. Then, seeds of the following weeds were sown in the soil, which was kept under wet conditions:

barnyard grass (Echinochloa);
flatsedge (Cyperus);
monochoria (Monochoria);
broad-leaved weeds such as false pimpernel (Lindernia), toothcup (Rotala), elatine (Elatine), ammannia (Ammannia), and dopatrium (Dopatrium); and Scirpus juncoides Roxb var. Hotarui Ohwi (Scirpus).

Then, water was supplied to each pot to a height of 2–3 cm above the soil surface. Five days after the transplantation of the rice plants, the emulsion of the active compound, which had been prepared in the manner mentioned above, was applied to the pots by water surface treatment. After that, the water depth was kept at about 3 cm.

Three weeks after the application of the active compound, the degree of damage to the weeds and the degree of phytotoxicity on the rice plants were determined, and recorded according to an assessment scale. In this scale, 100% indicates the complete death, and 0% indicates no herbicidal effect or no phytotoxicity.

The test results are shown in Table 1.

TABLE 1

| Active compound No. | Dosage of active compound (g/ha) | Herbicidal effect (%) | | | | | Phytotoxicity (%) rice |
|---|---|---|---|---|---|---|---|
| | | A | B | C | D | E | |
| 1 | 500 | 100 | 100 | 100 | 100 | 100 | 10 |
|   | 250 | 90 | 100 | 98 | 98 | 98 | 10 |
| 2 | 500 | 100 | 100 | 100 | 100 | 100 | 10 |
|   | 250 | 90 | 100 | 70 | 100 | 100 | 0 |
| 3 | 500 | 100 | 100 | 98 | 100 | 100 | 0 |
|   | 250 | 90 | 100 | 95 | 70 | 100 | 0 |
| cC | 500 | 0 | 0 | 0 | 0 | 0 | 0 | wherein A represents barnyard grass;
B represents flatsedge;
C represents Scirpus juncoides Roxb. var. Hotarui Ohwi
D represents monochoria; and
E represents broad-leaved weeds It will be understood that the specification and examples are illustrative but not limitative of the present invention and that other embodiments within the spirit and scope of the invention will suggest themselves to those skilled in the art.

What is claimed is:

1. A 1-(3,4-disubstituted phenyl)tetrazolinone of the formula

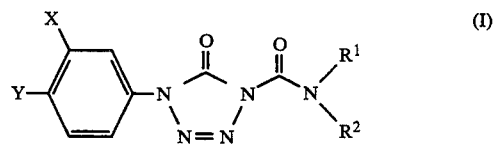

wherein
X represents halogen,
Y represents trifluoromethoxy or trifluoromethylthio,
$R^1$ represents propyl, isopropyl or allyl, and
$R^2$ represents propyl, isopropyl or allyl.

2. A compound according to claim 1, wherein
X represents fluorine or chlorine,
$R^1$ represents propyl or allyl, and
$R^2$ represents propyl or allyl.

3. A compound according to claim 2, wherein
X represents chlorine.

4. A compound according to claim 1, wherein such compound is 1-(3-chloro-4-trifluoromethoxyphenyl)-4-(N,N-dipropylcarbamoyl)-5(4H)-tetrazolinone of the formula

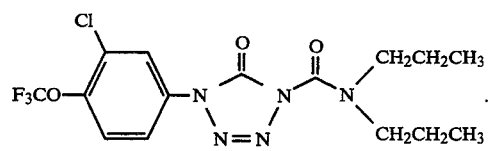

5. A compound according to claim 1, wherein such compound is 1-(3-chloro-4-trifluoromethylthiophenyl)-4-(N,N-dipropylcarbamoyl)-5(4H)-tetrazolinone of the formula

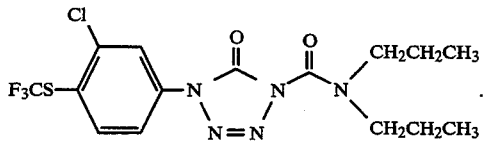

6. A compound according to claim 1, wherein such compound is 1-(3-chloro-4-trifluoromethoxyphenyl)-4-(N,N-diallylcarbamoyl)-5(4H)-tetrazolinone of the formula

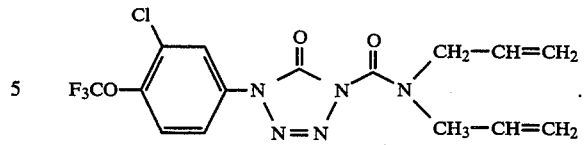

7. A herbicidal composition comprising a herbicidally effective amount of a compound according to claim 1 and a diluent.

8. A method of combatting unwanted vegetation which comprises applying thereto or to a locus from which it is desired to exclude such vegetation a herbicidally effective amount of a compound according to claim 1.

9. The method according to claim 8, wherein such compound is
1-(3-chloro-4-trifluoromethoxyphenyl)-4-(N,N-dipropylcarbamoyl)-5(4H)-tetrazolinone,
1-(3-chloro-4-trifluoromethylthiophenyl)-4-(N,N-dipropylcarbamoyl)-5(4H)-tetrazolinone or
1-(3-chloro-4-trifluoromethoxyphenyl)-4-(N,N-diallylcarbamoyl)-5(4H)-tetrazolinone.

* * * * *

UNITED STATES PATENT AND TRADEMARK OFFICE
CERTIFICATE OF CORRECTION

PATENT NO. : 5,344,814
DATED : September 6, 1994
INVENTOR(S) : Goto, et al.

It is certified that error appears in the above-indentified patent and that said Letters Patent is hereby corrected as shown below:

Title Page & Col. 1   Title [54]  Delete " HERBIDICAL "
line 1                and substitute -- HERBICIDAL --

Signed and Sealed this

Eleventh Day of June, 1996

*Attest:*

BRUCE LEHMAN

*Attesting Officer*   *Commissioner of Patents and Trademarks*